US007981165B2

(12) United States Patent
Simonet et al.

(10) Patent No.: US 7,981,165 B2
(45) Date of Patent: *Jul. 19, 2011

(54) PROCESS FOR LIGHTENING KERATIN MATERIALS USING AN ANHYDROUS COMPOSITION COMPRISING AT LEAST ONE FATTY SUBSTANCE AND AT LEAST ONE ALKALINE AGENT, AND AT LEAST ONE OXIDIZING COMPOSITION

(75) Inventors: Frédéric Simonet, Clichy (FR); Leïla Hercouet, Neuilly Plaisance (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/642,473

(22) Filed: Dec. 18, 2009

(65) Prior Publication Data
US 2010/0178263 A1 Jul. 15, 2010

Related U.S. Application Data

(60) Provisional application No. 61/147,841, filed on Jan. 28, 2009.

(30) Foreign Application Priority Data

Dec. 19, 2008 (FR) ..................... 08 58891

(51) Int. Cl.
D06L 3/02 (2006.01)
(52) U.S. Cl. ..................... 8/101; 8/107; 8/111
(58) Field of Classification Search .............. 8/101, 107, 8/111
See application file for complete search history.

(56) References Cited

U.S. PATENT DOCUMENTS

| 3,100,739 A | 8/1963 | Kaiser et al. |
| 3,369,970 A | 2/1968 | McLaughlin et al. |
| 3,629,330 A | 12/1971 | Brody et al. |
| 3,861,868 A | 1/1975 | Milbrada |
| 4,138,478 A | 2/1979 | Reese et al. |
| 4,170,637 A | 10/1979 | Pum |
| 4,226,851 A | 10/1980 | Sompayrac |
| 4,357,141 A | 11/1982 | Grollier et al. |
| 4,366,099 A | 12/1982 | Gaetani et al. |
| 4,488,564 A | 12/1984 | Grollier et al. |
| 4,725,282 A | 2/1988 | Hoch et al. |
| 4,826,681 A | 5/1989 | Jacquet et al. |
| 4,845,293 A | 7/1989 | Junino et al. |
| 5,021,066 A | 6/1991 | Aeby et al. |
| 5,259,849 A | 11/1993 | Grollier et al. |
| 5,364,414 A | 11/1994 | Lang et al. |
| 5,817,155 A | 10/1998 | Yasuda et al. |
| 6,010,541 A | 1/2000 | De La Mettrie |
| 6,074,439 A | 6/2000 | De La Mettrie et al. |
| 6,129,770 A | 10/2000 | Deutz et al. |
| 6,156,713 A | 12/2000 | Chopra et al. |
| 6,165,444 A | 12/2000 | Dubief et al. |
| 6,190,421 B1 | 2/2001 | Rondeau et al. |
| 6,206,935 B1 | 3/2001 | Onitsuka et al. |
| 6,238,653 B1 | 5/2001 | Narasimhan et al. |
| 6,251,378 B1 | 6/2001 | Laurent et al. |
| 6,260,556 B1 | 7/2001 | Legrand et al. |
| 6,277,154 B1 | 8/2001 | Lorenz |
| 6,277,155 B1 | 8/2001 | De La Mettrie et al. |
| 6,365,136 B1 | 4/2002 | Lauscher et al. |
| 6,423,100 B1 | 7/2002 | Lang et al. |
| 6,447,552 B1 | 9/2002 | Golinski |
| 6,645,258 B2 | 11/2003 | Vidal et al. |
| 6,660,045 B1 | 12/2003 | Hoeffkes et al. |
| 6,695,887 B2 | 2/2004 | Cottard et al. |
| 6,800,098 B1 | 10/2004 | Allard et al. |
| 7,135,046 B2 | 11/2006 | Audousset |
| 7,153,331 B2 | 12/2006 | Desenne et al. |
| 7,217,298 B2 | 5/2007 | Legrand et al. |
| 7,285,137 B2 | 10/2007 | Vidal et al. |
| 7,442,215 B2 | 10/2008 | Audousset et al. |
| 7,458,993 B2 | 12/2008 | Cottard et al. |
| 7,494,513 B2 | 2/2009 | Kravtchenko et al. |
| 7,575,605 B2 | 8/2009 | Legrand |
| 7,651,533 B2 | 1/2010 | Legrand |
| 7,651,536 B2 | 1/2010 | Cottard et al. |
| 7,740,663 B2 | 6/2010 | De La Mettrie et al. |
| 7,766,977 B2 | 8/2010 | Cottard |
| 7,799,095 B2 | 9/2010 | Mario et al. |

(Continued)

FOREIGN PATENT DOCUMENTS

CA  1 268 421  5/1990

(Continued)

OTHER PUBLICATIONS

Copending U.S. Appl. No. 12/339,753, filed Dec. 19, 2008.

(Continued)

Primary Examiner — Eisa B Elhilo
(74) Attorney, Agent, or Firm — Finnegan, Henderson, Farabow, Garrett & Dunner LLP

(57) ABSTRACT

The present disclosure relates to a process for lightening keratin fibers, comprising applying to the keratin fibers: an anhydrous composition (A) comprising at least one fatty substance in an amount of at least 20% by weight relative to the total weight of the composition, at least one surfactant, and at least one alkaline agent chosen from organic amines, organic amine salts, and ammonium salts; and a composition (B) comprising at least one oxidizing agent. The present disclosure also relates to a multi-compartment device comprising: a first compartment comprising the anhydrous composition (A); and a second compartment comprising the composition (B).

21 Claims, No Drawings

U.S. PATENT DOCUMENTS

| | | |
|---|---|---|
| 2003/0190297 A1 | 10/2003 | Narasimham et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0226110 A1 | 11/2004 | LeGrand |
| 2004/0235700 A1 | 11/2004 | Legrand et al. |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1* | 11/2006 | Kravtchenko et al. ............ 8/405 |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1* | 9/2008 | Syed et al. ......................... 8/111 |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 193 471 | 9/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 | 7/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 449 512 | 8/2006 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 473 | 1/2009 |
| EP | 2 011 474 | 1/2009 |
| EP | 2 018 848 | 1/2009 |
| EP | 2 072 034 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |

| | | |
|---|---|---|
| WO | WO 2005/055966 | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/010883 | 1/2009 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 20 05 076, dated Aug. 6, 1970.
English language Abstract of DE 38 14 356, dated Sep. 8, 1988.
English language Abstract of DE 43 09 509, dated Sep. 19, 1994.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 716 840, dated Nov. 2, 2006.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 892 623, dated May 4, 2007.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/096027, dated Aug. 30, 2007.
English language Abstract of WO 2007/006418, dated Jan. 18, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.

French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed in co-pending U.S. Appl. No. 12/339,753, dated Jul. 9, 2010.
Notice of Allowance mailed Jun. 11, 2010, in U.S. Appl. No. 12/642,489.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.
Copending U.S. Appl. No. 12/976,093, filed Dec. 22, 2010.
Copending U.S. Appl. No. 12/976,124, filed Dec. 22, 2010.
European Search Report for EP 10 15 5935, dated Oct. 8, 2010.
French Search Report for FR 09/59388, dated Aug. 3, 2010.
French Search Report for FR 09/59391, dated Sep. 16, 2010.
Notice of Allowance mailed Dec. 10, 2010, in U.S. Appl. No. 12/642,599.
Notice of Allowance mailed Dec. 14, 2010, in U.S. Appl. No. 12/642,551.
Notice of Allowance mailed Dec. 15, 2010, in U.S. Appl. No. 12/642,637.
Notice of Allowance mailed Dec. 20, 2010, in U.S. Appl. No. 12/642,531.
Notice of Allowance mailed Dec. 20, 2010, in U.S. Appl. No. 12/642,575.
Notice of Allowance mailed Dec. 28, 2010, in U.S. Appl. No. 12/642,536.
Notice of Allowance mailed Dec. 29, 2010, in U.S. Appl. No. 12/642,480.
Notice of Allowance mailed Dec. 29, 2010, in U.S. Appl. No. 12/642,555.
Notice of Allowance mailed Jan. 28, 2011, in U.S. Appl. No. 12/642,592.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Nov. 30, 2010, in U.S. Appl. No. 12/642,624.
Office Action mailed Dec. 17, 2010, in co-pending U.S. Appl. No. 12/642,451.
Office Action mailed Nov. 22, 2010, in co-pending U.S. Appl. No. 12/642,593.

* cited by examiner

PROCESS FOR LIGHTENING KERATIN MATERIALS USING AN ANHYDROUS COMPOSITION COMPRISING AT LEAST ONE FATTY SUBSTANCE AND AT LEAST ONE ALKALINE AGENT, AND AT LEAST ONE OXIDIZING COMPOSITION

This application claims benefit of U.S. Provisional Application No. 61/147,841, filed Jan. 28, 2009. This application also claims benefit of priority under 35 U.S.C. §119 to French Patent Application Nos. 0858891, filed Dec. 19, 2008.

The present disclosure relates to a process for lightening human keratin fibers such as the hair.

Processes for lightening keratin materials such as human keratin fibers consist of using an aqueous composition comprising at least one oxidizing agent, under alkaline pH conditions in the majority of cases. This oxidizing agent has the role of degrading the melanin of the hair, which, depending on the nature of the oxidizing agent present, leads to a more or less pronounced lightening of the fibers. Thus, for relatively weak lightening, hydrogen peroxide is used as the oxidizing agent. When greater lightening is sought, peroxygenated salts, for instance persulfates, are used as the oxidizing agent in the presence of hydrogen peroxide.

One of the difficulties arises from the fact that the lightening process is performed under alkaline conditions and the alkaline agent most commonly used is aqueous ammonia. Aqueous ammonia allows the pH of the composition to be adjusted to an alkaline pH that enables activation of the oxidizing agent. This agent also causes swelling of the keratin fiber, with raising of the scales, which promotes the penetration of the oxidizing agent into the fiber, and thus increases the efficacy of the reaction.

However, this basifying agent is volatile, which users find disagreeable due to the strong, rather unpleasant odor of ammonia that is given off during the process.

Furthermore, the amount of ammonia given off requires the use of higher contents than necessary in order to compensate for this loss. This is not without consequences on the user, who not only remains inconvenienced by the odor, but may also be confronted with greater risks of intolerance, for instance irritation of the scalp (stinging).

With respect to the option of replacing all or some of the aqueous ammonia with at least one other standard basifying agent, this does not lead to compositions that are as efficient as those based on aqueous ammonia, since these alkaline agents do not afford sufficient lightening of pigmented fibers in the presence of the oxidizing agent.

One objective of the present disclosure is to propose processes for lightening keratin materials, for example, keratin fibers such as the hair, which do not have the drawbacks of those used with existing compositions, due to the presence of large amounts of aqueous ammonia, while at the same time remaining at least as efficient, with respect to the lightening and the homogeneity of the lightening.

One aspect of the present disclosure is to provide a process for lightening keratin materials, comprising applying to the keratin fibers:
(a) an anhydrous composition (A) comprising at least one fatty substance in an amount greater than 20% by weight relative to the total weight of the composition, at least one surfactant, and at least one alkaline agent chosen from organic amines, organic amine salts, and ammonium salts; and
(b) a composition (B) comprising at least one oxidizing agents.

The present disclosure also relates to a multi-compartment device comprising, a first compartment comprising the anhydrous composition (A) and a second compartment comprising the composition (B).

The keratin materials treated by the process according to the present disclosure are, for example, the skin and the hair. The process of the present disclosure makes it possible to obtain a good level of lightening of keratin materials such as the hair, without giving off an odor of ammonia, which may be irritant.

The term "anhydrous composition," as used herein, means a cosmetic composition with a water content equal to 0% or less than 3% by weight, for example, less than 2% by weight or less than 1% by weight, relative to the weight of the anhydrous composition. The water present in the composition is more particularly may be "bound water," for instance the water of crystallization of salts, or traces of water absorbed by the starting materials used in the preparation of the anhydrous compositions according to the present disclosure.

In addition, in some embodiments, the anhydrous composition (A) does not comprise any direct dye or oxidation dye precursor (bases and couplers) used for the dyeing of human keratin fibers; or, if it does contain any, their total content does not exceed 0.005% by weight relative to the weight of the composition. At such a content, only the composition would be possibly dyed, no dyeing effect on the keratin fibers would be observed.

The anhydrous composition (A) comprises at least one fatty substance.

The term "fatty substance," as used herein, means an organic compound that is insoluble in water at ordinary temperature (25° C.) and at atmospheric pressure (760 mmHg). The solubility of fatty substance may be less than 5%, such as 1% or for example, 0.1%. They have in their structure at least one hydrocarbon-based chain comprising at least 6 carbon atoms or a sequence of at least two siloxane groups. In addition, the fatty substances may be soluble in organic solvents under the same temperature and pressure, for instance, they may be soluble in chloroform, ethanol, benzene, or decamethylcyclopentasiloxane.

The at least one fatty substance may be chosen from lower alkanes, fatty alcohols, fatty acids, fatty acid esters, fatty alcohol esters, oils, such as mineral, plant, animal, or synthetic non-silicone oils, non-silicone waxes, and silicones.

In some embodiments, the fatty alcohols, fatty esters, and fatty acids may contain at least one linear or branched, saturated or unsaturated hydrocarbon-based groups comprising 6 to 30 carbon atoms, which may be optionally substituted with at least one hydroxyl group (such as 1 to 4 hydroxyl groups). If they are unsaturated, these compounds may comprise one to three conjugated or non-conjugated carbon-carbon double bonds.

The alkanes may comprise from 6 to 16 carbon atoms and may be linear or branched, or optionally cyclic. By way of non-limiting example, the alkanes may be chosen from hexane, undecane, dodecane, tridecane, and isoparaffins, such as isohexadecane and isodecane.

Non-silicone oils that may be used in the composition of the present disclosure include but are not limited to:
hydrocarbon-based oils of animal origin, such as perhydrosqualene;
hydrocarbon-based oils of plant origin, such as liquid fatty acid triglycerides comprising from 6 to 30 carbon atoms (for instance heptanoic or octanoic acid triglycerides), or alternatively, for example, sunflower oil, corn oil, soybean oil, marrow oil, grapeseed oil, sesameseed oil, hazelnut oil, apricot oil, macadamia oil, arara oil, sunflower oil, castor oil, avocado oil, caprylic/capric acid triglycerides (for instance those sold by the company Stéarineries Dubois, or those sold under the names MIGLYOL® 810, 812 and 818 by the company Dynamit Nobel), jojoba oil, and shea butter oil;

linear or branched hydrocarbons of mineral or synthetic origin comprising from 6 to 16 carbon atoms (for instance, hexane, dodecane, or isohexadecane), or comprising more than 16 carbon atoms (such as liquid paraffins and derivatives thereof), or as additional examples, petroleum jelly, liquid petroleum jelly, and hydrogenated polyisobutenes such as PARLEAM®. As a non-limiting example, the oils may be chosen from liquid paraffins, petroleum jelly, liquid petroleum jelly, polydecenes, and hydrogenated polyisobutenes such as PARLEAM®;

partially hydrocarbon-based fluoro oils; fluoro oils that may also be mentioned include but not limited to, perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that may be used as fatty substances in the composition of the present disclosure may not be oxyalkylenated. They may be saturated or unsaturated, linear or branched and contain from 6 to 30 carbon atoms, such as from 8 to 30 carbon atoms. Non-limiting mention may be made of cetyl alcohol, stearyl alcohol, and the mixture thereof (cetylstearyl alcohol); octyldodecanol; 2-butyloctanol; 2-hexyldecanol; 2-undecylpentadecanol; oleyl alcohol; and linoleyl alcohol.

The non-silicone wax(es) that may be used in the composition of the present disclosure may be chosen from carnauba wax; candelilla wax; esparto grass wax; paraffin wax; ozokerites; plant waxes such as olive wax, rice wax, hydrogenated jojoba wax or the absolute waxes of flowers such as the essential wax of blackcurrant blossom sold by the company Bertin (France); animal waxes, for instance beeswaxes or modified beeswaxes (cerabellina); other waxes or waxy starting materials that may be used according to the present disclosure, for example, marine waxes such as the product sold by the company Sophim under the reference M82; and polyethylene waxes or polyolefin waxes.

The fatty acids that may be used in the composition of the present disclosure may be saturated or unsaturated and comprise from 6 to 30 carbon atoms such as from 9 to 30 carbon atoms. As non-limiting examples, they may be chosen from myristic acid, palmitic acid, stearic acid, behenic acid, oleic acid, linoleic acid, linolenic acid, and isostearic acid.

The esters may be chosen from esters of saturated or unsaturated, linear or branched C1-C26 aliphatic mono- or polyacids and of saturated or unsaturated, linear or branched C1-C26 aliphatic mono- or polyalcohols, the total carbon number of the esters may be greater than or equal to 10.

Among the monoesters, non-limiting mention may be made of dihydroabietyl behenate; octyldodecyl behenate; isocetyl behenate; cetyl lactate; C12-C15 alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates; 2-ethylhexyl palmitate; 2-octyldecyl palmitate; alkyl myristates such as isopropyl, butyl, cetyl, 2-octyldodecyl, myristyl, or stearyl myristate; hexyl stearate; butyl stearate; isobutyl stearate; dioctyl malate; hexyl laurate; and 2-hexyldecyl laurate.

In some embodiments, esters of C4-C22 dicarboxylic or tricarboxylic acids and of C1-C22 alcohols and esters of mono-, di- or tricarboxylic acids and of C2-C26 di-, tri-, tetra- or pentahydroxy alcohols may also be used.

In some embodiments, the following esters may be used: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

In some embodiments, the esters are chosen from ethyl, isopropyl, myristyl, cetyl, or stearyl palmitate; 2-ethylhexyl palmitate; 2-octyldecyl palmitate; alkyl myristates such as isopropyl, butyl, cetyl or 2-octyldodecyl myristate; hexyl stearate; butyl stearate; isobutyl stearate; dioctyl malate; hexyl laurate; 2-hexyldecyl laurate; isononyl isononanoate; and cetyl octanoate.

The composition may also comprise, as fatty ester, sugar esters and diesters of C6-C30 fatty acids such as of C12-C22 fatty acids. The term "sugar" means oxygen-bearing hydrocarbon-based compounds comprising several alcohol functions, with or without aldehyde or ketone functions, and which contain at least 4 carbon atoms. These sugars may be chosen from monosaccharides, oligosaccharides, or polysaccharides.

Non-limiting examples of sugars include sucrose (or saccharose), glucose, galactose, ribose, fucose, maltose, fructose, mannose, arabinose, xylose and lactose, and derivatives thereof (for example, alkyl derivatives, such as methyl derivatives, for instance methylglucose).

The sugar esters of fatty acids may be chosen from the group comprising the esters or mixtures of esters of sugars described previously, and of linear or branched, saturated or unsaturated C6-C30 fatty acids such as C12-C22 fatty acids. If they are unsaturated, these compounds may comprise one to three conjugated or nonconjugated carbon-carbon double bonds.

In some embodiments, the esters may be chosen from mono-, di-, tri-, tetraesters, and polyesters.

These esters may also be chosen, for example, from oleates, laurates, palmitates, myristates, behenates, cocoates, stearates, linoleates, linolenates, caprates, and arachidonates, or mixtures thereof such as oleo-palmitate, oleo-stearate, and palmito-stearate mixed esters.

In some embodiments, monoesters and diesters such as sucrose, glucose, or methylglucose mono- or dioleates, stearates, behenates, oleopalmitates, linoleates, linolenates, and oleostearates may be used.

A non-limiting example that may be mentioned is the product sold under the name GLUCATE® DO by the company Amerchol, which is a methylglucose dioleate.

Non-limiting examples of esters or mixtures of esters of sugar and of fatty acid include:

the products sold under the names F160, F140, F110, F90, F70 and SL40 by the company Crodesta, respectively denoting sucrose palmitostearates formed from 73% monoester and 27% diester and triester; from 61% monoester and 39% diester, triester and tetraester; from 52% monoester and 48% diester, triester and tetraester; from 45% monoester and 55% diester, triester and tetraester; from 39% monoester and 61% diester, triester and tetraester; and sucrose monolaurate;

the products sold under the name RYOTO SUGAR ESTERS, for example referenced B370 and corresponding to sucrose behenate formed from 20% monoester and 80% di-triester-polyester;

the sucrose mono-dipalmito-stearate sold by the company Goldschmidt under the name TEGOSOFT® PSE.

The silicones that may be used in the composition of the present disclosure may be volatile or non-volatile, cyclic, linear or branched silicones, which may be unmodified or modified with organic groups, having a viscosity ranging from 5×10-6 to 2.5 m2/s at 25° C., such as 1×10-5 to 1 m2/s.

The silicones that may be used in accordance with the present disclosure may be in the form of oils, waxes, resins, or gums.

In some embodiments, the silicone is chosen from polydialkylsiloxanes such as polydimethylsiloxanes (PDMS), and organomodified polysiloxanes comprising at least one functional group chosen from poly(oxyalkylene) groups, amino groups, and alkoxy groups.

The organopolysiloxanes are defined in Walter Noll's "Chemistry and Technology of Silicones" (1968) Academic Press. They can be volatile or non-volatile.

When they are volatile, the silicones may be chosen from those having a boiling point of between 60° C. and 260° C., for example, they may be chosen from:

(i) cyclic polydialkylsiloxanes comprising from 3 to 7, for example, from 4 to 5 silicon atoms. These are, for example, octamethylcyclotetrasiloxane sold under the name VOLATILE SILICONE® 7207 by Union Carbide or SILBIONE® 70045 V2 by Rhodia; decamethylcyclopentasiloxane sold under the name VOLATILE SILICONE® 7158 by Union Carbide, and SILBIONE® 70045 V5 by Rhodia, and mixtures thereof.

Non-limiting mention may also be made of cyclocopolymers of the dimethylsiloxane/methylalkylsiloxane type, such as VOLATILE SILICONE® FZ 3109 sold by the company Union Carbide, of formula:

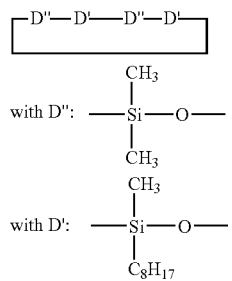

Non-limiting mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane.

Further examples of volatile silicones include (ii) linear volatile polydialkylsiloxanes comprising 2 to 9 silicon atoms and having a viscosity of less than or equal to $5\times10^{-6}$ m$^2$/s at 25° C. A non-limiting example is decamethyltetrasiloxane sold under the name SH 200 by the company Toray Silicone. Silicones belonging to this category are also described in the article published in Cosmetics and Toiletries, Vol. 91, Jan. 76, pp. 27-32, Todd & Byers "Volatile Silicone Fluids for Cosmetics".

Non-volatile polydialkylsiloxanes, polydialkylsiloxane gums and resins, polyorganosiloxanes modified with organofunctional groups above, and mixtures thereof, may be used.

These silicones may be chosen from polydialkylsiloxanes, for example, polydimethylsiloxanes containing trimethylsilyl end groups. The viscosity of the silicones is measured, for example, at 25° C. according to ASTM standard 445 Appendix C.

Among these polydialkylsiloxanes, mention may be made, in a nonlimiting manner, of the following commercial products:

the SILBIONE® oils of the 47 and 70 047 series or the MIRASIL® oils sold by Rhodia, for instance the oil 70 047 V 500 000;

the oils of the MIRASIL® series sold by the company Rhodia;

the oils of the 200 series from the company Dow Corning, such as DC200 with a viscosity of 60 000 mm$^2$/s;

the VISCASIL® oils from General Electric and certain oils of the SF series (SF 96, SF 18) from General Electric.

Non-limiting mention may also be made of polydimethylsiloxanes comprising dimethylsilanol end groups known under the name Dimethiconol (CTFA), such as the oils of the 48 series from the company Rhodia.

In this category of polydialkylsiloxanes, mention may also be made of the products sold under the names ABIL WAX® 9800 and 9801 by the company Goldschmidt, which are poly(C1-C20)dialkylsiloxanes.

The silicone gums that can be used in accordance with the present disclosure may be chosen from polydialkylsiloxanes, for example, polydimethylsiloxanes with high number-average molecular weight ranging from 200 000 to 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane, and tridecane, or mixtures thereof.

Products that can be used in accordance with the present disclosure are mixtures, such as:

mixtures formed from a polydimethylsiloxane hydroxylated at the chain end, or dimethiconol (CTFA), and from a cyclic polydimethylsiloxane also known as cyclomethicone (CTFA), such as the product Q2 1401 sold by the company Dow Corning;

mixtures formed from a polydimethylsiloxane gum with a cyclic silicone, such as the product SF 1214 SILICONE FLUID from the company General Electric; this product is an SF 30 gum corresponding to a dimethicone, having a number-average molecular weight of 500 000, dissolved in the oil SF 1202 SILICONE FLUID corresponding to decamethylcyclopentasiloxane;

mixtures of two PDMSs with different viscosities, for instance, mixtures of a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5\times10^{-6}$ m$^2$/s. This product may contain 15% SE 30 gum and 85% SF 96 oil.

The organopolysiloxane resins that can be used in accordance with the present disclosure include but not limited to, crosslinked siloxane systems containing the following units:

$R_2SiO_{2/2}$, $R_3SiO_{1/2}$, $RSiO_{3/2}$ and $SiO_{4/2}$ wherein R is chosen from alkyl groups containing 1 to 16 carbon atoms, for instance, R is chosen from $C_1$-$C_4$ lower alkyl radicals such as methyl.

Among these resins, non-limiting mention may be made of the product sold under the name DOW CORNING 593 or those sold under the names SILICONE FLUID SS 4230 and SS 4267 by the company General Electric, which are silicones of dimethyl/trimethyl siloxane structure.

Non-limiting mention may also be made of the trimethyl siloxysilicate type resins sold under the names X22-4914, X21-5034 and X21-5037 by the company Shin-Etsu.

The organomodified silicones that can be used in accordance with the present disclosure may be chosen from silicones as defined above and comprising in their structure at least one organofunctional group attached via a hydrocarbon-based radical.

Besides the silicones described above, the organomodified silicones may be polydiarylsiloxanes, such as polydiphenylsiloxanes, and polyalkylarylsiloxanes functionalized with the organofunctional groups mentioned previously.

The polyalkylarylsiloxanes may be chosen from linear and/or branched polydimethyl/methylphenylsiloxanes and polydimethyl/diphenylsiloxanes with a viscosity ranging from $1 \times 10^{-5}$ to $5 \times 10^{-2}$ m2/s at 25° C.

Among these polyalkylarylsiloxanes, examples that may be mentioned include but not limited to, the products sold under the following names:

the SILBIONE® oils of the 70 641 series from Rhodia;

the oils of the RHODORSIL® 70 633 and 763 series from Rhodia;

the oil DOW CORNING 556 COSMETIC GRADE FLUID from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Among the organomodified silicones, non-limiting mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248, or the oils SILWET® L 722, L 7500, L 77, and L 711 by the company Union Carbide, and the ($C_{12}$)alkylmethicone copolyol sold by the company Dow Corning under the name Q2 5200;

substituted or unsubstituted amine groups, such as the products sold under the name GP 4 SILICONE FLUID and GP 7100 by the company Genesee; or the products sold under the names Q2 8220 and DOW CORNING 929 or 939 by the company Dow Corning. The substituted amine groups may be chosen from $C_1$-$C_4$ aminoalkyl groups;

alkoxylated groups such as the product sold under the name SILICONE COPOLYMER F-755 by SWS Silicones, and ABIL WAX® 2428, 2434, and 2440 by the company Goldschmidt.

In some embodiments, the at least one fatty substances may be chosen from compounds that are liquid or pasty at room temperature and at atmospheric pressure.

In some embodiments, the at least one fatty substance may be chosen from compounds that are liquid at a temperature of 25° C. and at atmospheric pressure.

In some embodiments, the at least one fatty substance is other than fatty acids.

In some embodiments, the at least one fatty substance may be chosen from lower alkanes, fatty alcohols, fatty acid esters, fatty alcohol esters, oils (such as mineral, plant, or synthetic non-silicone oils), and silicones.

In some embodiments, the at least one fatty substance of the composition according to the present disclosure is chosen from non-silicone oils.

According to one embodiment, the at least one fatty substance is chosen from liquid petroleum jelly, polydecenes, and liquid esters of fatty acids or of fatty alcohols, or mixtures thereof; for example, the at least one fatty substance of the composition according to the present disclosure is chosen from non-silicone oils. In some embodiments, the at least one fatty substance is non-oxyalkylenated or non-glycerolated.

The anhydrous composition (A) comprises at least 20% fatty substance. For example, the at least one fatty substance is present in an amount ranging from 20% to 95%, such as ranging from 40% to 80% of the total weight of the composition.

The anhydrous composition (A) also comprises at least one surfactant.

In some embodiments, the at least one surfactant is chosen from nonionic surfactants and anionic surfactants.

The anionic surfactants may be chosen from the salts (for instance, alkali metal salts such as sodium salts; ammonium salts; amine salts; amino alcohol salts; or alkaline-earth metal salts such as magnesium salts) of the following compounds:

alkyl sulfates, alkyl ether sulfates, alkylamido ether sulfates, alkylaryl polyether sulfates, monoglyceride sulfates;

alkylsulfonates, alkylamidesulfonates, alkylarylsulfonates, α-olefin sulfonates, paraffin sulfonates;

alkyl phosphates, alkyl ether phosphates;

alkylsulfosuccinates, alkyl ether sulfosuccinates, alkylamidesulfosuccinates; alkylsulfosuccinates;

alkylsulfoacetates;

acylsarcosinates; acylisethionates and N-acyltaurates;

salts of fatty acids such as oleic acid, ricinoleic acid, palmitic acid or stearic acid, coconut oil acid or hydrogenated coconut oil acid;

alkyl-D-galactoside uronic acid salts;

acyllactylates;

salts of polyoxyalkylenated alkyl ether carboxylic acids, of polyoxyalkylenated alkylaryl ether carboxylic acids or of polyoxyalkylenated alkylamido ether carboxylic acids, such as those comprising from 2 to 50 ethylene oxide groups;

and mixtures thereof.

The alkyl or acyl radical of these various compounds may comprise from 6 to 24 carbon atoms, such as from 8 to 24 carbon atoms; and the aryl radical may be chosen from phenyl and benzyl groups.

The nonionic surfactants may be chosen from, for example, monooxyalkylenated or polyoxyalkylenated, monoglycerolated or polyglycerolated nonionic surfactants. The oxyalkylene units may be chosen from, for instance, oxyethylene and oxypropylene units, or a combination thereof. For example, the oxyalkylene units may be oxyethylene units.

Examples of oxyalkylenated nonionic surfactants include but not limited to:

oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyethylenated esters of saturated or unsaturated, linear or branched, $C_8$-$C_{30}$ acids and of sorbitol, saturated or unsaturated, oxyethylenated plant oils, condensates of ethylene oxide and/or of propylene oxide, inter alia, alone or as mixtures.

These surfactants may comprise a number of moles of ethylene oxide and/or of propylene oxide ranging from 1 to 50 moles, such as ranging from 2 to 30 moles. Further as a non-limiting example, the nonionic surfactants do not comprise any oxypropylene units.

In some embodiments, the oxyalkylenated nonionic surfactants may be chosen from oxyethylenated C8-C30 alcohols, such as oxyethylenated C18-C30 alcohols.

Non-limiting examples of ethoxylated fatty alcohols that may be mentioned include adducts of ethylene oxide with lauryl alcohol, such as those comprising from 9 to 50 oxyethylene groups, for instance, those comprising from 10 to 12 oxyethylene groups (laureth-10 to laureth-12 in CTFA names); adducts of ethylene oxide with behenyl alcohol, such as those comprising from 9 to 50 oxyethylene groups (beheneth-9 to beheneth-50 in CTFA names); adducts of ethylene oxide with cetostearyl alcohol (mixture of cetyl alcohol and stearyl alcohol), such as those comprising from 10 to 30 oxyethylene groups (ceteareth-10 to ceteareth-30 in CTFA names); adducts of ethylene oxide with cetyl alcohol, such as those comprising from 10 to 30 oxyethylene groups (ceteth-10 to ceteth-30 in CTFA names); adducts of ethylene oxide with stearyl alcohol, such as those comprising from 10 to 30 oxyethylene groups (Steareth-10 to Steareth-30 in CTFA names); adducts of ethylene oxide with isostearyl alcohol, such as those comprising from 10 to 50 oxyethylene groups (Isosteareth-10 to Isosteareth-50 in CTFA names); and mixtures thereof.

Examples of ethoxylated fatty acids that may be mentioned include the adducts of ethylene oxide with lauric, palmitic, stearic or behenic acid, and mixtures thereof, such as those comprising from 9 to 50 oxyethylene groups, such as PEG-9 to PEG-50 laurates (CTFA names: PEG-9 laurate to PEG-50 laurate); PEG-9 to PEG-50 palmitates (CTFA names: PEG-9 palmitate to PEG-50 palmitate); PEG-9 to PEG-50 stearates (CTFA names: PEG-9 stearate to PEG-50 stearate); PEG-9 to PEG-50 palmitostearates; PEG-9 to PEG-50 behenates (CTFA names: PEG-9 behenate to PEG-50 behenate); and mixtures thereof.

Mixtures of these oxyethylenated derivatives of fatty alcohols and of fatty acids may also be used.

In some embodiments, the anhydrous composition (A) comprises at least one ethoxylated fatty alcohol.

As non-limiting examples of monoglycerolated or polyglycerolated nonionic surfactants, monoglycerolated or polyglycerolated C8-C40 alcohols may be used.

In some embodiments, the monoglycerolated or polyglycerolated C8-C40 alcohols correspond to the following formula:

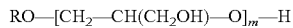

RO—[CH$_2$—CH(CH$_2$OH)—O]$_m$—H wherein R is chosen from linear or branched $C_8$-$C_{40}$ alkyl or alkenyl radicals, such as $C_8$-$C_{30}$ alkyl or alkenyl radicals, and m is chosen from a number ranging from 1 to 30 such as from 1 to 10.

As non-limiting examples of compounds that may be suitable in accordance with the present disclosure, non-limiting mention may be made of lauryl alcohol comprising 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may be chosen from mixtures of alcohols in the same way that the value of m represents a statistical value, which means that, in a commercial product, several species of polyglycerolated fatty alcohol may coexist in the form of a mixture.

The monoglycerolated or polyglycerolated alcohols may be chosen from the C8/C10 alcohols comprising 1 mol of glycerol, the C10/C12 alcohol comprising 1 mol of glycerol, and the C12 alcohol comprising 1.5 mol of glycerol.

The at least one surfactant in the anhydrous composition (A) may be present in an amount ranging from 0.1% to 50% by weight such as ranging from 0.5% to 30% by weight relative to the weight of the anhydrous composition.

The anhydrous composition (A) of the present disclosure may further comprise at least one alkaline agent.

The at least one alkaline agent may be chosen from organic amines and organic amine salts.

The organic amines may be chosen from the ones having a pKb at 25° C. of less than 12, such as less than 10 or such as less than 6. It should be noted that this is the pKb corresponding to the function of highest basicity.

Organic amines may be chosen from organic amines comprising one or two primary, secondary, or tertiary amine functions, and at least one linear or branched C1-C8 alkyl groups bearing at least one hydroxyl radical.

Organic amines may also be chosen from alkanolamines such as mono-, di- or trialkanolamines, comprising one to three identical or different C1-C4 hydroxyalkyl radicals.

Among the compounds of this type that may be mentioned include but not limited to: monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, and tris(hydroxymethylamino)methane.

The organic amines having the following formula:

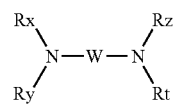

wherein W is chosen from $C_1$-$C_6$ alkylene residues optionally substituted with a hydroxyl group or a $C_1$-$C_6$ alkyl radical; Rx, Ry, Rz and Rt, which may be identical or different, are chosen from a hydrogen atom, $C_1$-$C_6$ alkyl radicals, $C_1$-$C_6$ hydroxyalkyl radicals, and $C_1$-$C_6$ aminoalkyl radicals.

Examples of such amines that may be mentioned include but not limited to: 1,3-diaminopropane, 1,3-diamino-2-propanol, spermine, and spermidine.

In some embodiments, the organic amines are chosen from amino acids.

As non-limiting examples, the amino acids that may be used may be of natural or synthetic origin, in L, D, or racemic form, and comprise at least one acid function chosen from, for instance, carboxylic acid, sulfonic acid, phosphonic acid, and phosphoric acid functions. The amino acids may be in their neutral or ionic form.

Further as non-limiting examples, the amino acids may be chosen from basic amino acids comprising an additional amine function optionally included in a ring or in a ureido function.

Such basic amino acids may be chosen from those corresponding to formula (I) below:

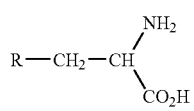
(I)

wherein R is a group chosen from:

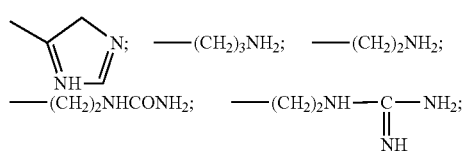

The compounds corresponding to formula (I) may be chosen from histidine, lysine, arginine, ornithine, and citrulline.

Amino acids that may be used in the present disclosure include but not limited to: aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

In some embodiments, the organic amines are chosen from basic amino acids. The amino acids may be chosen from, for instance, arginine, lysine and histidine, or mixtures thereof.

In some embodiments, the organic amines are chosen from organic amines of heterocyclic type. Besides histidine that has already been mentioned in the amino acids, non-limiting mention may also be made of pyridine, piperidine, imidazole, 1,2,4-triazole, tetrazole, and benzimidazole.

In some embodiments, the organic amines are chosen from amino acid dipeptides. Amino acid dipeptides that may be used in the present disclosure include but not limited to: carnosine, anserine, and baleine.

In some embodiments, the organic amines are chosen from compounds comprising a guanidine function. Organic amines of this type that may be used in the present disclosure include, besides arginine that has already been mentioned as an amino acid, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

As a non-limiting example, the organic amines are chosen from alkanolamines. For example, the organic amines are chosen from 2-amino-2-methyl-1-propanol and monoethanolamine, or mixtures thereof. Further as an example, the organic amine is monoethanolamine.

The alkaline agent may be an organic amine in salt form. The term "organic amine salt," as used herein, means organic or mineral salts of an organic amine as described above.

As a non-limiting example, the organic salts may be chosen from the salts of organic acids, such as citrates, lactates, glycolates, gluconates, acetates, propionates, fumarates, oxalates and tartrates.

Further as a non-limiting example, the mineral salts may be chosen from hydrohalides (for example hydrochlorides), carbonates, hydrogen carbonates, sulfates, hydrogen phosphates, and phosphates.

The ammonium salts that may be used in the anhydrous composition (A) according to the present disclosure may be chosen from the following acid salts: carbonate, bicarbonate. For instance, the salt is the carbonate, such as ammonium carbonate.

In some embodiments, the composition comprises ammonia or a salt thereof, and the amount of basifying agent(s) is greater than that of ammonia (expressed as NH3).

In some embodiments, the anhydrous composition (A) comprises at least one alkaline agent in an amount ranging from 0.1% to 40% by weight, such as from 0.5% to 20% by weight relative to the weight of said composition.

In some embodiments, the anhydrous composition comprises at least one water-soluble organic solvent. Non-limiting examples of water-soluble organic include: linear or branched C2-C4 alkanols, such as ethanol and isopropanol; polyols and polyol ethers, for instance 2-butoxyethanol, glycerol, propylene glycol, dipropylene glycol, polyethylene glycols, propylene glycol monomethyl ether or diethylene glycol monomethyl ether or monoethyl ether, and also aromatic alcohols such as benzyl alcohol or phenoxyethanol, and mixtures thereof. The term "water-soluble solvent," as used herein, means a compound that is liquid at 25° C. and at atmospheric pressure (760 mmHg), and it has a solubility of at least 5% in water under these conditions.

The anhydrous composition (A) may also contain various adjuvants conventionally used in hair lightening compositions, such as anionic, cationic, nonionic, amphoteric, or zwitterionic polymers, or mixtures thereof; mineral thickeners, for example, fillers such as clays, talc; organic thickeners with, for example, anionic, cationic, non-ionic, and amphoteric polymeric associative thickeners; antioxidants; penetrants; sequestrants; fragrances; dispersants; film-forming agents; preserving agents; opacifiers.

In some embodiments, the anhydrous composition comprises at least one stabilizing polymer. The at least one stabilizing polymer may be chosen from cellulose-based polymers such as nonionic, cationic, or anionic cellulose ethers, for example, cationic cellulose ethers. These stabilizing polymers may be associative or non-associative. Non-associative cellulose ethers that may be mentioned include but not limited to, hydroxyethylcellulose and hydroxypropylcellulose. The associative cellulose ethers that may be mentioned include but not limited to, cetylhydroxyethyl celluloses.

In some embodiments, the anhydrous composition (A) is an oil-in-water-soluble solvent(s) direct emulsion.

The process is performed with a composition (B) comprising at least one oxidizing agent.

In some embodiments, the at least one oxidizing agent is chosen from hydrogen peroxide, urea peroxide, alkali metal bromates or ferricyanides, and peroxygenated salts, for instance alkali metal or alkaline-earth metal persulfates, perborates peracids and precursors thereof, and percarbonates.

In some embodiments, the at least one oxidizing agent is constituted by hydrogen peroxide, for example, as an aqueous solution (aqueous hydrogen peroxide solution), the titre of which may range from 1 to 40 volumes (0.3 to 12% of H2O2) or may range from 5 to 40 volumes (1.5 to 12% of H2O2).

In some embodiments, the composition (B) (1.5% to 12% H2O2) may also comprise, besides hydrogen peroxide, an additional oxidizing agent chosen from peroxygenated salts.

Composition (B) may be an aqueous composition. As used herein, the term "aqueous composition" means a composition comprising at least 20% by weight of water, such as at least 30% by weight of water, for instance, at least 40% by weight of water.

This composition (B) may also comprise at least one water-soluble organic solvent as described above. It may also comprise at least one acidifying agent.

Non-limiting examples of acidifying agents include mineral or organic acids, for instance hydrochloric acid, orthophosphoric acid, sulfuric acid, carboxylic acids, for instance acetic acid, tartaric acid, citric acid or lactic acid, and sulfonic acids.

In some embodiments, the pH of the composition (B) is less than 7.

Finally, the composition (B) can be in various forms, for instance a solution, an emulsion, or a gel.

The process of the present disclosure may be performed by applying the anhydrous composition (A) and the composition (B) successively and without intermediate rinsing, the order being irrelevant.

In some embodiments, a composition obtained by extemporaneously mixing, at the time of use, of the anhydrous composition (A) and of the composition (B) is applied to wet or dry keratin materials. According to this embodiment, the weight ratio of the amounts of (A)/(B) ranges from 0.1 to 10, for example, from 0.2 to 2 such as from 0.3 to 1.

In some embodiments, after mixing together the compositions (A) and (B) described previously, the amount of at least one fatty substance is greater than 20% by weight, for example, greater than 25% by weight such as greater than 30% by weight, relative to the weight of the mixture of the compositions (A) and (B).

In some embodiments, the mixture present on the keratin materials (resulting either from the extemporaneous mixing of (A) and (B) or from the partial or total successive application thereof) is left in place for a time, from about 1 minute to 1 hour, for example, from 5 minutes to 30 minutes.

The temperature during the process may range from room temperature (from 15 to 25° C.) to 80° C., such as from room temperature to 60° C.

After the treatment, the keratin materials may be optionally rinsed with water, optionally washed, and then rinsed with water, before being dried or left to dry.

In some embodiments, the keratin materials are human hair.

Finally, the disclosure relates to a multi-compartment device comprising first compartment comprising the anhydrous composition (A); and a second compartment comprising the composition (B); the anhydrous composition (A) and composition (B) having been described previously.

EXAMPLES

Example 1

The following composition was prepared:

| Composition A1 | g % |
| --- | --- |
| Pure monoethanolamine | 4 |
| Glycerol | 45 |
| Polyglycerolated (6 mol) lauryl cetylstearyl glycol sold under the name Chimexane NS | 1% |
| Liquid petroleum jelly | 50% |

At the time of use, composition A1 (oil-in-water-soluble solvent direct emulsion) was mixed with an equal amount (in weight) of an aqueous oxidizing composition containing 20 volumes of $H_2O_2$ and at pH 2.2.

The mixture was then applied to a lock of natural chestnut-brown hair (tone depth=4). The "mixture/lock" bath ratio was 10/1 (g/g). The leave-on time was 30 minutes at 27° C. After this time, the locks were rinsed, and then washed with ELVIVE multivitamin shampoo, rinsed, and dried.

Example 2

The following composition was prepared:

| Composition A2 | g % |
| --- | --- |
| Pure monoethanolamine | 4 |
| Liquid petroleum jelly | 50 |
| PEG-8 | 32 |
| Hydroxypropylcellulose Klucel EF Pharm sold by Aqualon | 4 |
| Oleth-10 | 10 |

At the time of use, composition A2 was mixed with an equal weight of aqueous oxidizing composition (B2) containing 20 volumes of $H_2O_2$ and at pH 2.2.

The mixture was then applied to a lock of natural chestnut-brown hair (tone depth=4). The "mixture/lock" bath ratio was, respectively, 10/1 (g/g). The leave-on time was 30 minutes at 27° C. After this time, the locks were rinsed, and then washed with ELVIVE multivitamin shampoo, rinsed and dried.

Results

Emulsions A1 and A2 of the disclosure did not give off any aggressive odor. Furthermore, the level of lightening obtained with the emulsions of the present disclosure was acceptable, being of the same level as that of conventional ammonia-based lightening compositions.

What is claimed is:

1. A process for lightening keratin fibers, comprising applying to the keratin fibers:
   (a) an anhydrous composition (A) comprising at least one fatty substances in an amount of at least 20% by weight relative to the total weight of the anhydrous composition (A), at least one surfactant, and at least one alkaline agent chosen from organic amines, organic amine salts, and ammonium salts; and
   (b) a composition (B) comprising at least one oxidizing agent.

2. The process according to claim 1, wherein the at least one fatty substance in the anhydrous composition (A) is in an amount ranging from 40% to 80% by weight, relative to the weight of the anhydrous composition (A).

3. The process according to claim 1, wherein the at least one fatty substance is chosen from compounds that are liquid or pasty at room temperature and at atmospheric pressure.

4. The process according to claim 1, wherein the at least one fatty substance is chosen from $C_6$-$C_{16}$ alkanes, non-oxyalkylenated fatty alcohols, fatty acids, fatty acid esters, fatty alcohol esters, mineral oils of at least 16 carbon atoms, plant non-silicone oils, animal non-silicone oils, synthetic non-silicone oils, silicones, and non-silicone waxes.

5. The process according to claim 1, wherein the at least one fatty substance is chosen from liquid petroleum jelly, polydecenes, liquid esters of fatty acids, and liquid esters of fatty alcohols.

6. The process according to claim 1, wherein the at least one surfactant in the anhydrous composition (A) is chosen from nonionic surfactants.

7. The process according to claim 6, wherein the nonionic surfactants are chosen from monooxyalkylenated nonionic surfactants, polyoxyalkylenated nonionic surfactants, monoglycerolated nonionic surfactants, and polyglycerolated nonionic surfactants.

8. The process according to claim 1, wherein the organic amines are chosen from alkanolamines and basic amino acids.

9. The process according to claim 8, wherein the alkanolamines are chosen from 2-amino-2-methyl-1-propanol and monoethanolamine.

10. The process according to claim 8, wherein the basic amino acids are chosen from arginine, histidine, and lysine.

11. The process according to claim 1, wherein the anhydrous composition (A) further comprises at least one cellulose ether chosen from associative cellulose ethers and non-associative cellulose ethers.

12. The process according to claim 1, wherein the anhydrous composition (A) further comprises at least one water-soluble solvent.

13. The process according to claim 12, wherein the anhydrous composition (A) is an anhydrous oil-in-water-soluble solvent direct emulsion.

14. The process according to claim 1, wherein the at least one oxidizing agent in the aqueous composition (B) is chosen from hydrogen peroxide, urea peroxide, alkali metal bromates, alkali metal ferricyanides, peroxygenated salts, percarbonates of alkali metals, and percarbonates of alkaline-earth metals.

15. The process according to claim 14, wherein the peroxygenated salts are chosen from persulfates, perborates, peracids, and precursors thereof.

16. The process according to claim 14, wherein the at least one oxidizing agent is hydrogen peroxide.

17. The process according to claim 1, wherein the composition (B) comprises at least 20% by weight of water, relative to the total weight of the composition.

18. The process according to claim 1, wherein the anhydrous composition (A) and composition (B) are mixed together before applying to the keratin fibers.

19. The process according to claim 1, wherein the anhydrous composition (A) and the aqueous composition (B) are applied to the keratin fibers successively and without intermediate rinsing.

20. The process according to claim 1, wherein the keratin fibers are human hair.

21. A multi-compartment device comprising:
a first compartment comprising the anhydrous composition (A) according to claim 1; and
a second compartment comprising the composition (B) according to claim 1.

* * * * *